United States Patent [19]
Eaton et al.

[11] 3,982,997
[45] Sept. 28, 1976

[54] IMMOBILIZED GLUCOSE ISOMERASE

[75] Inventors: David L. Eaton; Ralph A. Messing, both of Horseheads, N.Y.

[73] Assignee: Corning Glass Works, Corning, N.Y.

[22] Filed: Sept. 18, 1974

[21] Appl. No.: 507,209

[52] U.S. Cl. .............................. 195/31 F; 195/63; 195/68; 195/DIG. 11; 195/116
[51] Int. Cl.² ..................... C07G 7/02; C12D 13/00
[58] Field of Search ....... 195/31 F, 63, 68, DIG. 11, 195/116

[56] References Cited
UNITED STATES PATENTS
3,847,740  11/1974  Heady et al..................... 195/63 X
3,868,304  2/1975  Messing........................... 195/31 F

*Primary Examiner*—David M. Nafe
*Attorney, Agent, or Firm*—James A. Giblin; Clinton S. Janes, Jr.; Clarence R. Patty, Jr.

[57] ABSTRACT

An efficient immobilized glucose isomerase composite can be prepared by adsorbing the enzyme within the pores of a porous inorganic support having an average pore size between about 100 Å and 1000 Å and consisting of about 0.84% to 12.0% MgO and 99.16% to 88.0% $Al_2O_3$, by weight.

13 Claims, No Drawings

IMMOBILIZED GLUCOSE ISOMERASE

BACKGROUND OF THE INVENTION

1. Field

This invention is concerned generally with the immobilization of catalytically active enzymes onto essentially water insoluble carrier materials. Specifically, the invention is concerned with the adsorption of glucose isomerase onto the internal surfaces of a high surface area, porous inorganic support consisting of mixed metal oxides of MgO and $Al_2O_3$.

Because of the catalytic specificity of enzymes, considerable attention has been directed toward finding methods of using them in both laboratory and industrial applications. Enzymes are commonly water-soluble, and, for that reason, many enzymes are uneconomical to use in large scale batch-type operations since the enzymes can generally be used only one time in the absence of rather costly enzyme recovery and purification steps. In recent years, however, techniques have been devised to fix active enzymes on essentially water-insoluble support materials that can be readily removed from a reaction, thus permitting re-use of the insolubilized or immobilized enzyme. This disclosure describes a novel immobilized glucose isomerase composite demonstrating a high degree of enzymatic activity per unit weight of composite.

2. Prior Art

Glucose isomerase is an enzyme which catalyzes the isomerization of the sugar glucose to the sugar fructose, sometimes referred to as levulose. The desirability of converting glucose to fructose is well recognized for various reasons. For example, although fructose has the same caloric value as glucose, it is a sweeter sugar. Thus, with fructose, a fixed sweetness can be achieved at a relatively lower caloric intake. Further, the sugar glucose is relatively abundant from a variety of sources and, hence, available as a raw material source for fructose production.

It has been well known that glucose can be isomerized to fructose by both alkaline and enzymatic methods. The alkaline isomerization of glucose solution requires subjecting a glucose-containing solution to an alkaline environment in which isomerization to fructose can occur. Unfortunately, the alkaline isomerization of glucose to fructose has been unsatisfactory, generally because of the tendency of non-selective alkaline catalysts to produce undesirable by-products which adversely affect the product taste and which are difficult to remove. Among the known undesirable byproducts of alkaline isomerization are various color bodies and acidic products which require added processing steps for removal. Some of the disadvantages associated with alkaline isomerization have been overcome by the relatively recent discovery that finely divided alumina may be used in an alkaline environment to isomerize glucose. As disclosed in U.S. Pat. No. 3,431,253, by using alkaline alumina (>pH 7) having a large surface area, it has been found possible to avoid formation of objectionable by-products. A further disclosed advantage is that by using solid alumina particles, the alumina can easily be removed from a reaction medium and reused. Unfortunately, however, the use of finelydivided alumina requires a relatively long residence time for the glucose solution, thus tending to preclude more economical continuous or flow-through reactions. Further, because of a suspected equilibrium which exists between glucose and fructose, the optimum conversion of glucose to fructose is limited under the batch-type reaction conditions disclosed in the above patent.

Because of the problems associated with alkaline isomerization, increasing attention is being directed toward enzymatic isomerization methods using glucose isomerase. As used herein, glucose isomerase refers to that enzyme or enzyme system which catalyzes the isomerization of glucose to fructose, regardless of enzyme source. The enzyme itself can be derived from a variety of organisms (e.g., U.S. Pat. No. 3,813,318) and numerous methods are known for extracting and purifying glucose isomerase. The use of soluble glucose isomerase preparations for large scale commercial fructose manufacture is generally limited due to enzyme cost for one-time use and/or costs associated with recovery or inactivation of the spent soluble enzyme. For those reasons, recent attention has been directed toward finding methods of immobilizing enzymes on high surface area, essentially water-insoluble carrier materials, both organic and inorganic.

There are a number of disadvantages associated with the use of organic carriers as enzyme support materials. For example, many organics are subject to microbrial attack, especially during long term use. Further, some of the organics tend to swell in an aqueous environment, thus posing pressure problems in continuous use column operations. Further yet, many organics lack a very high surface area needed to assure maximum enzyme loading and, because of their organic nature, many such carriers are difficult to sterilize by conventional methods. Many of the above disadvantages have been overcome by recent discoveries showing that certain inorganic materials can be used as enzyme support materials.

Methods of adsorbing various enzymes to a number of siliceous materials are disclosed in U.S. Pat. No. 3,556,945. Methods of chemically coupling enzymes to a wide variety of inorganics through an intermediate silane coupling agent are disclosed in U.S. Pat. No. 3,519,538. More recently in patent application S.N. 332,807, filed Feb. 16, 1973, now U.S. Pat. No. 3,850,751, entitled "Enzymes Immobilized on Porous Inorganic Support Materials", filed in the name of R. A. Messing and assigned to the present assignee, it was disclosed that very efficient immobilized enzyme composites could be prepared by bonding the enzyme to the internal surface of porous ceramic materials having an average pore diameter of less than 1000 A, preferably less than about 500 A or between about 100 A and 500 A. By choosing an average pore diameter at least as large as the size of the enzyme but less than about 1000 A, it was disclosed that a high surface area for high enzyme loading is provided and that the internally bonded enzymes tended to be protected from detachment, especially in turbulent reaction environments.

In U.S. Pat. application Ser. No. 332,739, filed Feb. 16, 1973, now U.S. Pat. No. 3,868,304, in the name of R. A. Messing, entitled "Method of Making Fructose with Immobilized Glucose Isomerase", and assigned to the present assignee, there is disclosed a method of isomerizing glucose to fructose using a composite consisting of glucose isomerase adsorbed to porous alumina bodies having an average pore size ranging from about 100 A to 1000 A. As disclosed in the above-cited patent application, it is known that various metal ions are needed in the enzymatic isomerization of glucose to fructose. See, for example, an article by Y. Takasaki et al., entitled, "Studies on Sugar-Isomerizing Enzyme, Purification, Crystallization and Some Properties of Glucose Isomerase from *Streptomyces sp.*", in *Agr. Biol. Chem.*, Vol. 33, No. 11, p. 1527–34 (1969). In that article, the effects of various metal ions such as Mg, Co, Fe, Mn, Ni, Ba, Ca, Zn, and Cu, were examined with the conclusion that glucose isomerase from a cited *Streptomyces sp.* strain requires the presence of both cobalt and magnesium ions for its activity. Typically, the presence of those and other ions is assured by adding them to the glucose feed prior to contact with an immobilized enzyme system, as shown by the examples of Ser. No. 332,739. The addition of various metal ions to the glucose feed material requires added processing steps in the production of fructose with immobilized glucose isomerase, especially in a continuous flow-through reactor (e.g. plug-flow column). Further, when such ions are added to the feed solution, they become a part of the final product. This is especially undesirable in the case of ions such as those of cobalt. Because of the undesirability of having such ions in the final product, especially food products, and because of added costs associated with the removal of such ions, there has been a recognized need for providing an immobilized glucose isomerase system which assures the presence of needed metal ions and yet avoids the problems associated with past systems.

Quite surprisingly, it has been found that apparently a portion of the metal ion requirements of an immobilized glucose isomerase system and the critical pH parameters of such a system can be simultaneously met with a porous inorganic carrier material having a very critical metal oxide composition range, described in detail below.

SUMMARY OF INVENTION

The essence of the present invention is the discovery that a very high enzyme loading per gram of carrier for an immobilized glucose isomerase composite can be achieved by incorporating a critical amount of MgO in a porous $Al_2O_3$ enzyme support material. Specifically, it has been found that a very efficient immobilized glucose isomerase composite can be prepared by adsorbing glucose isomerase enzymes to the internal surfaces of a high surface area (at least 5 $m^2/g$), porous, inorganic carrier having an average pore diameter ranging from about 100 A to about 1000 A and comprising by weight, between 0.84% and 12.0% MgO and 99.16% and 88.0% $Al_2O_3$, preferably comprising between about 0.84% and about 3.80% MgO. In very preferred embodiments, the porous MgO—$Al_2O_3$ enzyme carrier is in particulate form having an average particle size between about 4 and 200 mesh, U.S. Standard Sieve, preferably between 30 and 45 mesh with the average pore diameter being between about 150 A and 250 A. Methods of preparing the carrier, the immobilized glucose isomerase composite, and methods of using the composite to prepare fructose are disclosed hereunder.

The method of using the immobilized glucose isomerase composite to partially isomerize the glucose in a glucose containing solution involves the step of reacting an aqueous glucose solution under isomerizing conditions with the composite. Preferably, the composite consists of glucose isomerase molecules adsorbed to the internal surfaces of a plurality of porous particles having an average particle size between about 4 and 200 mesh, the composite being contained in a plugged flow-through column through which the glucose solution, containing at least 10% by weight glucose, is continuously passed under isomerizing conditions. Very preferably, the pH of the glucose solution, prior to passage through the column is between about 7.0 and 9.0, more preferably between 7.4 and 8.8, with the inorganic support consisting by weight of between about 0.84 and 3.80% MgO and 99.16 and 96.2% $Al_2O_3$, and having an average pore diameter of between about 150 A and 250 A and an average particle size within the range of about 30 to 45 mesh, U.S. Standard Sieve.

SPECIFIC EMBODIMENTS

The essence of the present invention lies in the chemical and physical properties of the glucose isomerase carrier and its use to immobilize the enzyme for the production of fructose from a glucose solution. Specifically, it has been found that the amount of MgO in the MgO—$Al_2O_3$ porous carrier is critical in providing a high surface area support having an optimum pH and loading ability for the glucose isomerase enzymes and which may also partially satisfy the enzymes' metal ion requirements. It should be stressed that the carrier of the present invention is an improvement over that disclosed in Ser. No. 332,739, cited and discussed above. In that patent application, incorporated herein by reference thereto, it was pointed out that the average pore diameter of the porous $Al_2O_3$ should be between about 100 A and 1000 A, very preferably between about 140 A and 220 A. Because of slight differences in the manufacture of the Carriers of the present invention, which call for the addition of a critical amount of MgO, it has been found that the preferred average pore diameter is in the range of 150 A to 250 A. The specific improvement over the carrier of the above patent application lies in the discovery that magnesium ions which are essential for the glucose isomerase can be incorporated in the porous alumina carrier, as in the form of a magnesium oxide, such that magnesium is in close proximity to the glucose isomerase adsorbed to the carrier surface. Although the exact mechanism whereby magnesium assists the catalytic action of glucose isomerase is not fully understood, it has been found that at least four distinct advantages result when small, controlled quantities of MgO are incorporated into the porous alumina matrix:

1. the microenvironment pH within the porous body support and the pH of the substrate or feed can be controlled with respect to the enzyme needs.
2. the quantity of active glucose isomerase immobilized can be increased substantially over and above any activity associated with surface pretreatment with magnesium ions or incorporation of magnesium ions within the feed.
3. the enzyme utilization factor or bonding efficiency can be enhanced with respect to the amount of magnesium in the porous carrier.
4. the enzyme half-life can be extended.

It has been discovered that the critical range, by weight, of MgO in the MgO—$Al_2O_3$ carrier required to bring about the overall improvements is between about 0.84% and 12.0%. Preferably the amount of MgO ranges between 0.84% and 3.80% and it was found that a very useful carrier is provided when the amount of MgO is in the narrow range of between 2.0% and 2.4%.

Specifically, it has been found that when the amount of MgO is below 0.84%, the adsorptive ability of the carrier decreases significantly whereas above 12.0% MgO, the enzymatic activity decreases. Both effects are related to the MgO content of the porous carrier and/or its subsequent effect on microenvironment pH, as shown in the examples below.

The porous inorganic enzyme carrier consisting essentially of varying amounts of $Al_2O_3$ and MgO can be prepared in a variety of ways. As shown in Ser. No. 332,807, however, it has been found that the average pore diameter of the inorganic carrier should be at least as large as its enzyme but less than about 1000 A, very preferably, less than about 500 A or, if possible, between about 100 A and 500 A. In the case of glucose isomerase and the present carriers, it has been found that the preferred average pore diameter should be between about 150 A and 250 A. Accordingly, in the examples below, specific directions are given for preparing porous $MgO—Al_2O_3$ carriers having an average pore diameter within that range. Further directions are given for fixing the glucose isomerase onto the carriers to form immobilized glucose isomerase composites. Methods are also described for using the immobilized glucose isomerase to isomerize glucose to fructose.

The general method for preparing the $MgO—Al_2O_3$ porous carriers involves starting with alumina particles having an average particle size of about 300 A ±200 A. These particles are then mixed with a solution consisting of varying amounts or concentrations of magnesium ions to form a slurry which is mixed well. The magnesium ions can be added from a variety of available sources such as $MgCl_2 \cdot 6H_2O$ or $Mg(OH)_2$. The slurry is then gently dried to remove water. This drying step tends to shrink the individual particles together such that the ultimate dried product is porous and has an average pore size approximating the average particle size of the starting materials. The gentle drying can be accomplished via a number of methods such as simple air drying, drying with gentle heat (~100°C), spray drying the slurry, and like methods. The main requirement in the drying step is that it be gentle enough to preserve the skeletal pore structure formed as the particles shrink together.

After drying, the porous body is strengthened by firing it to a temperature below the sintering point; e.g., fired to about 400° to 600°C for about 1 to 16 hours.

The resulting product can then be comminuted, if necessary, and the individual porous particles sorted according to desired mesh size range which is desirably between 4 and 200 mesh, preferably between 30 and 45 mesh, U.S. Standard Sieve. Alternatively, the slurry can be spray dried to the desired particle size range prior to firing.

After the porous particles are prepared, they can be used to immobilize the glucose isomerase molecules by adsorption to internal surfaces of the porous bodies. By using porous particles having an average pore diameter of less than 1000 A, in particle sizes of 30 to 45 mesh, a very high surface area per gram (e.g., greater than about 5 m²/g) is assured for maximum enzyme loading. We have found that enzyme loading is increased significantly if, prior to adsorption of the enzymes, the carriers reacted with an aqueous citrate solution (e.g. 0.1 molar citric acid or sodium citrate solution, pH 7.0).

The general enzyme adsorption procedure involves mixing the porous particles with an aqueous glucose isomerase solution consisting of between about 1 and 2 ml of enzyme preparation per gram of washed, wet porous carrier. Preferably the enzyme preparation is very concentrated and contains from about 1000 to about 5000 IGIU per ml. Preferably, the adsorption step is for at least 2 hours, depending on such factors as porous particle size, enzyme solution concentration and the like. Once the enzyme is so immobilized, the resulting composite can be stored, preferably in water, or as a moist cake until used.

In use, the composite is reacted with a glucose-containing solution buffered to a pH range in which optimum isomerization occurs. The pH should be adjusted to between 7.0 and 9.0, preferably between 7.4 and 8.8. Various buffers, known to those skilled in the art, may be used in the glucose solution.

In a preferred continuous processing system, the composite particles are placed in a plugged flow-through column (30 to 45 mesh particles, having an average pore diameter between 150 A and 250 A) through which a buffered solution containing at least about 10% by weight glucose is continuously passed. Preferably, the concentration of the glucose solution is at least about 30% by weight. Flow rate through the column is adjusted to assure maximum isomerization; e.g., about 42% to 50% conversion of the glucose to fructose.

Preferred methods for making the carrier and immobilized enzymes are given below. The alumina particles used to form the $MgO—Al_2O_3$ porous bodies were obtained commercially and had the following characteristics:

Surface area: 100 ±20 m²/g
Avg. particle diameter (A): 300 ±200
pH of aqueous 10% by wt. suspension: 4.4
Specific gravity: 3.6 g/cc
Note: X-ray studies indicate about 90% gamma alumina The soluble glucose isomerase source was a crude preparation containing about 2700 International Glucose Isomerase Units (IGIU) per ml where one IGIU represents the enzyme activity needed to produce one $\mu$m mole fructose per min. at 60°C., pH 6.85 from a 2 M glucose solution. After the enzymes were immobilized it was found that the optimum pH range for the isomerization was between 7.4 and 8.8 and, because of the upper pH limit, the amount of MgO in the carrier must be limited to no more than about 12.0% by weight as shown below. The relative amounts of MgO in each carrier were determined by wet chemical analysis or flame spectroscopy. Assays of enzymatic activity for each enzyme composite were performed in a modified manner to reflect use of a non-soluble enzyme and activity changes which would be encountered in a commercial application. Thus, for all composites, the performance of the immobilized enzymes packed in a 1.5 cm diameter column was observed at 60°C. using a 50% (wt.) glucose feed (Cerelose, cation exchanged) at pH 8.4 containing 0.005 M $MgCl_2$. Activity was calculated as $$E = 27.9 \left(\frac{F}{W}\right) \ln \left(\frac{1}{1-x/x_e}\right)$$

where $E$ = Activity units, $F$ = flow rate (ml/hr), $W$ = Immobilized enzyme wt (g, day basis), $x$ = % Fructose and $x_e$ = % fructose at equilibrium (51.2%).

Preparation of Carriers Having Varying Amts. of MgO

Ten sample carriers were made consisting of alumina and from 0 to 28.6% MgO (by weight). The respective ingredients and particle shapes of each sample carrier are shown in Table I, below. By using the amounts shown in the table, the sample carriers were made by first adding to the indicated amounts of distilled or deionized water sufficient glacial acetic acid to bring the solution to 0.1 Molar. Then a slurry was formed by adding the indicated amounts of the alumina with vigorous stirring. The stirring was continued until a smooth, creamy mixture was obtained, approximately 15–30 minutes. The pH was then adjusted to 2.0 to 3.0 and the indicated magnesium compound was added to the slurry mixture either as a liquid, or as a solid. This mixture was then blended at a high speed for an additional period of time, about 15–30 minutes. The resulting blend was then formed into particles or spheres, as indicated, by either slip casting or spray drying, respectively. The slip cast material was then broken and sorted according to indicated particle size by conventional means. Both the slip cast and spray dried material were fired at 600°C for 16 hrs. Prior to adsorption of the enzymes, the effect of MgO additions on the "pH" of the carriers was determined by mixing 1 gram of each carrier with 9 grams of distilled water for about 15 minutes to achieve an equilibrium, and then measuring the pH of the mixture with a conventional pH meter.

sents a normalized value associated with an increased loading observed using the irregularly shaped particles (cf. spheres).

TABLE II

Activity/gram v. % MgO + Carrier pH + Carrier Shape

| Sample No. | % MgO | pH | Shape | $E_o$ | $E_{o\ (equiv.)}$ |
|---|---|---|---|---|---|
| 1 | 0 | 4.4 | Spheres | 203 | 203 |
| 2 | 0 | 4.4 | Particles | 387 | (200) |
| 3 | 0.84 | 7.0 | Particles | 805 | (600) |
| 4 | 1.4 | 7.5 | Spheres | 650 | (650) |
| 5 | 2.2 | 8.2 | Spheres | 898 | 898 |
| 6 | 2.9 | 8.1 | Spheres | 899 | 899 |
| 7 | 3.8 | 8.4 | Spheres | 909 | 909 |
| 8 | 6.65 | 8.8 | Particles | 916 | (720) |
| 9 | 12.0 | 8.9 | Particles | 768 | (600) |
| 10 | 28.6 | 9.3 | Particles | 200 | ( 50) |

To be commercially feasible, the immobilized glucose isomerase should have an enzymatic loading of at least about 500 units of activity per gram of carrier under a continuous isomerization (flow through) process. As can be seen from Table II, this loading level is obtained when the % by weight MgO in the MgO—$Al_2O_3$ porous carrier is within the range of about 0.84 to about 12.0% MgO with best results obtained when the carrier consisted of about 0.84 to 3.8% MgO. Although the exact mechanism(s) whereby the MgO content results in improved loading is not fully understood, it can be appreciated from the data in Table II that the carrier pH may play a role in determining loading

TABLE I (Porous Bodies)

| Sample No. | Ingredients | | | | Final Product | | |
|---|---|---|---|---|---|---|---|
| | Amt. $H_2O$ | Amt. $Al_2O_3$ | Amt. $MgCl_2.6H_2O$ | Amt. $Mg(OH_2)$ | Carrier Shape | pH | % MgO(wt.) |
| | | | | | (30–45 mesh) | | |
| 1* | 489 | 400 | 0 | 0 | Spheres | 4.4 | 0 |
| 2** | 100 | 100 | 0 | 0 | Particles | 4.4 | 0 |
| 3** | 100 | 99.16 | 4.3 | 0 | Particles | 7.0 | 0.84 |
| 4* | 244 | 200 | 14.2 | 0 | Spheres | 7.5 | 1.4 |
| 5* | 244 | 200 | 22.3 | 0 | Spheres | 8.2 | 2.2 |
| 6* | 244 | 200 | 29.4 | 0 | Spheres | 8.1 | 2.9 |
| 7* | 244 | 200 | 38.6 | 0 | Spheres | 8.4 | 3.8 |
| 8** | 100 | 100 | 0 | 10.3 | Particles | 8.8 | 6.65 |
| 9** | 100 | 100 | 69.2 | 0 | Particles | 8.9 | 12.0 |
| 10** | 100 | 100 | 0 | 58.1 | Particles | 9.3 | 28.6 |

*pounds
**grams
Note:
All Porous Bodies had an average pore diameter within the range of 150 to 250A and an average particle size of 30–45 mesh.

Immobilization of the Enzymes

Each of the above carrier samples was used to immobilize the glucose isomerase by reacting the enzyme preparation with each carrier to adsorb the enzyme onto the internal surfaces of the pores. The amount of enzyme preparation used corresponded to about 15 ml of the enzyme preparation for each 15 grams of carrier. Prior to the actual adsorption step, each carrier sample was initially washed with distilled water by fluidizing the carrier sample in a column. The washed carriers were then reacted with a 0.1 Molar citrate solution in a shaking bath for one hour. Then, the enzyme preparation was added and the adsorption was allowed to proceed for about 24 hours with shaking to facilitate the adsorption process. The final product was then rinsed with distilled water and the individual samples were assayed as indicated above with the following results where $E_o$ represents the enzymatic activity per gram determined as described above and $E_o$ (equiv) repreamount since the desired minimum loading of at least 500 activity units per gram occurs on carriers having a pH within the range of 7.0 to 8.9. Hence, it is thought that the addition of MgO may not only serve to satisfy a portion of the enzymes $Mg^{++}$ needs but also set carrier ph parameters which limit both higher and lower loadings. From the above data, however, it can be concluded that the amount of MgO in the porous MgO—$Al_2O_3$ carrier is indeed critical and that the critical amount of MgO is within the range of about 0.84 to 12.0% by wt., preferably within the range of about 0.84 to about 3.8%.

From the above examples, it can be seen that the porous inorganic carriers provide an excellent high surface area support for an adsorbed glucose isomerase system. Inasmuch as the above-disclosed carriers, composites, and methods for making fructose are subject to minor variations by those skilled in the art, it is intended that the above examples should be construed as merely illustrative of various preferred embodiments and that the scope of the present invention should be limited by the appended claims.

We claim:

1. An immobilized enzyme composite comprising glucose isomerase adsorbed to the internal surfaces of a high surface area porous inorganic support material having an average pore diameter between about 100 A and 1000 A and consisting of between 0.84 and 12.0% MgO and 99.16% and 88.0% $Al_2O_3$ by weight.

2. The composite of claim 1 wherein the support material is in particulate form having an average particle size between about 4 and 200 mesh, U.S. Standard Sieve.

3. The composite of claim 1 wherein the support material has an average pore diameter between about 150 A and 250 A.

4. The composite of claim 2 wherein the support material consists of between about 0.84% and 3.8% MgO and 99.16% and 96.2% $Al_2O_3$ by weight.

5. The composite of claim 2 wherein the support material has an average particle size between about 30 and 45 mesh, U.S. Standard Sieve, and average pore diameter between about 150 A and 250 A, and consists of between about 0.84% and 3.8% MgO and 99.16% and 96.2% $Al_2O_3$ by weight.

6. A method of partially isomerizing a glucose solution to a fructose solution which comprises the steps of reacting the glucose solution at a pH between about 7.0 and 9.0 with an immobilized enzyme composite consisting of glucose isomerase molecules adsorbed to the internal surface of a high surface area, porous inorganic support material having an average pore diameter between about 100A and 1000A and consisting, by weight, of between 0.84 to 12.0% MgO and about 99.16% to 88.0% $Al_2O_3$.

7. The method of claim 6 wherein the porous inorganic support material consists of a plurality of particles having an average particle size between about 4 and 200 mesh, U.S. Standard Sieve, the particles being contained in a plugged flow-through column through which a glucose solution is continuously passed.

8. The method of claim 7 wherein the particles have an average pore diameter between about 150 A and 250 A.

9. The method of claim 7 wherein the particles consist of between about 0.84 and 3.8% MgO and about 99.16 and 96.2% $Al_2O_3$, by weight.

10. The method of claim 7 wherein particles have an average particle size between about 30 and 45 mesh U.S. Standard Sieve.

11. The method of claim 6 wherein the pH is between about 7.4 and 8.8.

12. The method of claim 7 wherein the particles consist by weight of between about 0.84 and 3.8% MgO and 99.16 and 96.2% $Al_2O_3$, have an average particle size between about 30 and 45 mesh, U.S. Standard Sieve, and average pore diameter between about 150 A and 250 A, and, prior to passage through the column, the pH of the glucose solution is between about 7.0 and 9.0.

13. The method of claim 12 wherein prior to passage through the column the pH of the glucose solution is between about 7.4 and 8.8.

* * * * *